United States Patent [19]

Thys-Jacobs

[11] Patent Number: 4,946,679

[45] Date of Patent: Aug. 7, 1990

[54] METHOD FOR THE TREATMENT OF PREMENSTRUAL SYNDROME

[76] Inventor: Susan Thys-Jacobs, 135 Hickory Grove Dr., Larchmont, N.Y. 10538

[21] Appl. No.: 414,620

[22] Filed: Sep. 29, 1989

Related U.S. Application Data

[63] Continuation of Ser. No. 223,498, Jul. 25, 1988, abandoned.

[51] Int. Cl.$^5$ ............... A01N 59/06; A01N 59/26
[52] U.S. Cl. ...................... 424/682; 424/687; 424/602; 424/678; 514/899
[58] Field of Search ............... 424/128, 154, 156; 514/899

[56] References Cited

U.S. PATENT DOCUMENTS

| | | | |
|---|---|---|---|
| 3,077,437 | 2/1963 | Heckel | 167/74 |
| 3,608,075 | 9/1971 | Glen et al. | 424/238 |
| 3,639,599 | 2/1972 | Merhof et al. | 424/239 |
| 4,035,504 | 7/1977 | Baldwin | 514/450 |
| 4,076,811 | 2/1978 | Lachnit-Fixson et al. | 424/239 |
| 4,145,416 | 3/1979 | Lachnit-Fixson et al. | 424/319 |
| 4,241,087 | 12/1980 | Mir et al. | 514/596 |
| 4,291,028 | 9/1981 | Nichols | 514/178 |
| 4,315,033 | 2/1982 | Lawrason | 424/319 |
| 4,372,951 | 2/1983 | Nichols | 514/170 |
| 4,415,554 | 11/1983 | Horrobin | 424/145 |
| 4,439,432 | 3/1984 | Peat | 424/195 |
| 4,497,800 | 2/1985 | Larson et al. | 424/157 |
| 4,542,026 | 9/1985 | Rios | 514/345 |
| 4,650,668 | 3/1987 | Barron et al. | 514/474 |
| 4,738,856 | 4/1988 | Clark | 514/574 |

OTHER PUBLICATIONS

*Handbook of Non-Prescription Drugs*, 1979, 6th edition, pp. 239-245.
Frank, R. T., 1931, Arch Neurol. Psychiatr. 26: 1053.
Seikus, P. 1988, Better Nutrition 50(2): 14-15.
Reid, R. L., et al., 1981, Am. J. Obstet, Gynecol. 139(1):86-97.
Price, W. A., et al., 1985, Resident and Staff Physician 31(5): 35.
Israel, S. L., 1938, JAMA 110: 721.
Zondek, B., and Brezezinski, A., 1948, Br., J. Obstet., Gynecol. 55: 273.
Argonz, J., and Abinzano, C., 1950, J. Clin. Endocrinol. Metab. 10: 1579.
London, R. S., et al., 1983, J. Am. Coll. Nutr. 2: 115-22.
Kendall, K. E., et al., 1987, Obstet. and Gynecol. 70(2): 145-149.
Greenhill, J. P., and Fried, S. C., 1941, JAMA 117: 504.
Muse, K. N., et al., 1984, N. Engl. J. Med. 311: 1345-1349.
Sheikh, M. S. et al., 1987, N. Engl. J. Med. 317: 532-536.
Maddocks, S. et al., 1986, Am. J. Obstet., Gynecol, 154(3): 573-581.

*Primary Examiner*—Dale R. Ore
*Attorney, Agent, or Firm*—Pennie & Edmonds

[57] ABSTRACT

A method for the treatment of premenstrual syndrome (PMS) by administering a therapeutically effective dose of calcium to an individual manifesting symptoms of PSM. Calcium may be administered in any appropriate form and manner. In a randomized, double-blind crossover placebo-controlled study of 33 women PMS symptomology was reduced on calcium treatment during both the luteal and the menstrual phases.

6 Claims, No Drawings

METHOD FOR THE TREATMENT OF PREMENSTRUAL SYNDROME

This is a continuation of application Ser. No. 223,498, filed July 25, 1988 now abandoned.

INTRODUCTION

The present invention is directed to a method for the treatment of premenstrual syndrome (PMS) with calcium. The method of the invention involves treating an individual who exhibits symptoms of PMS with a therapeutically effective dose of calcium.

The invention is illustrated by way of example, using a randomized, double-blind crossover study which was conducted in 33 women to evaluate the efficacy of calcium supplementation in PMS. PMS symptomatology was assessed by the daily recording of fourteen symptoms as well as by an overall retrospective analysis. The study established that calcium supplementation significantly reduced PMS symptomatology.

Although calcium supplementation is a simple and effective treatment for PMS, its precise role in PMS is unknown.

BACKGROUND OF THE INVENTION

Frank first described "premenstrual tension syndrome" (PMS) nearly 60 years ago (Frank, R. T. 1931, Arch. Neurol. Psychiatr. 26: 1053-1057).

Since then, PMS has been characterized by a number of both physical and psychological symptoms. It has recently been labeled a significant medical condition (Seikus, P., 1988, Better Nutrition 50(2): 14-15). PMS is defined as a psychoneuro-endocrine disorder encompassing a wide variety of symptoms. These symptoms regularly occur during the luteal phase of the menstrual cycle and usually abate after the menstrual flow begins. Symptoms can range from mild to incapacitating in severity. It has been estimated that as many as 20 to 50 percent of all regularly menstruating women experience moderate to severe PMS symptoms during their reproductive years. (Reid, R. L., et al., 1981, Am. J. Obstet. Gynecol. 139(1): 86). Some studies report that 100 percent of women experience some mild symptoms during this period.

The common symptoms of PMS include breast swelling and tenderness, tension, anxiety, emotional lability, irritability, fatigue, abdominal bloating and cramps, headache, backache, edema of the hands, ankles and face, nausea and vomiting, difficulty in sleeping, increased thirst or appetite and craving for high-carbohydrate foods, increased or decreased libido, and acneiform eruptions. Women with severe PMS have been shown to possess higher levels of neurotic behavior and trait anxiety than those with less severe symptoms. (Price, W. A., et al., 1985, Resident and Staff Physician 31(5): 35.

Numerous hypotheses have been advanced to explain the pathophysiology of PMS. The hypotheses include hormonal imbalances, hormonal deficiencies, vitamin deficiencies, hypoglycemia, endogenous hormone allergy, psychosomatic dysfunction, fluid retention and withdrawal imbalance, and alteration of endogenous opiates.

In 1931, Frank attributed the signs and symptoms of PMS to excess estrogen. Data to support Frank's hypothesis of an excessive estrogen effect have been inconclusive and contradictory. Subsequently, Israel (1938, JAMA 110: 721) suggested that a deficiency of progesterone leading to an unopposed estrogenic effect was responsible for PMS. Evidence that it was progesterone withdrawal as opposed to progesterone deficiency led workers in the 1950's to propose the administration of progesterone or testosterone to combat the effects of PMS. Progestin treatment remains popular today although its efficacy has never been demonstrated satisfactorily.

The use of vitamin $B_6$ therapy was first advocated in the 1940's. Vitamin $B_6$ has been shown (1) to correct deficient estrogen metabolism, and (2) to play a role in the regulation of the synthesis of dopamine and serotonin within the brain. However, following a study in which Zondek and Brezezinski (1948, Br. J. Obstet. Gynaecol. 55: 273) demonstrated normal estrogen levels in women with severe vitamin B deficiency, and numerous studies which failed to demonstrate a significant and consistent dopaminergic effect of vitamin $B_6$, this explanation for PMS has lost popularity.

Vitamin A was for a time implicated in the etiology of PMS. Hypothesizing that vitamin A might play a role in correcting aberrant estrogen metabolism, Argonz and Abinzano (1950, J. Clin. Endocrinol. Metab. 10: 1579) successfully treated 30 PMS patients with large doses of vitamin A. Vitamin A was thought to reduce PMS symptoms through opposition to thyroid hyperfunction or by exerting a direct antiestrogenic or diuretic effect.

The role of vitamin therapy in PMS awaits further clarification, but it is now thought that the existence of a cyclic vitamin deficiency in PMS patients is unlikely. While some researchers have continued to explore the role of vitamins, including vitamin E (London, R. S., et al., 1983, J. Am. Coll. Nutr. 2:115-22), other workers have even called for caution in the use of vitamin $B_6$ as a treatment for PMS (Kendall, K. E., et al., 1987, Obstet. and Gynecol. 70(2): 145-149).

Increased carbohydrate tolerance in the premenstruum has been said to account for the craving for sweets evidenced in some PMS patients. Reactive hypoglycemia, also once thought to be linked to the cause of PMS symptoms, cannot be linked to the cause of PMS symptoms other than the occasional craving for sweets seen in some women. Certain evidence suggests that when it does occur reactive hypoglycemia is usually asymptomatic and has been observed in subjects who show no signs of PMS as well as those demonstrating classical symptoms of PMS (Reid, R. L., et al., 1981, Am. J. Obstet. Gynecol. 139(1): 88).

Endogenous hormone allergy has also been said to play a role in PMS. However, this theory remains suspect given the unreliable nature of skin testing procedures employed in past studies.

Psychosomatic disorders or psychic factors are now widely believed to follow physiological, biochemical or anatomical changes resulting from hormonal effects. Still, psychotherapy and/or the use of a variety of tranquilizing agents have in the past been found to be only somewhat effective in treating PMS.

In 1941, Greenhill and Fried (1941, JAMA, 117: 504) proposed that sodium retention induced by ovarian steroids was the lone factor responsible for all of the symptom of PMS. They believed that Frank's success in treating PMS using cathartics was based upon their acting to eliminate excess estrogen through their dehydrating effect. Since then, diuretics have been alleged to be an effective treatment for PMS. No study, to date, has appropriately shown the improvement of PMS symptomatology using diuretics.

Current research has implicated a number of neurotransmitters and hormones as markers or etiologic agents. One promising area of research involves the endorphins-endogenous opioid peptides. Several prominent symptoms of PMS, e.g. nervousness, restlessness, cramps, nausea and vomiting are similar to the symptoms of opiate withdrawal. This similarity has led workers to hypothesize that beta-endorphin withdrawal or imbalance may be responsible for many of the PMS symptoms. This hypothesis is further supported by one study which showed that the administration of naloxone, an opiate antagonist, was less effective in treating PMS than placebo. Furthermore, the withdrawal of endorphins, which is known to vary with estrogen levels, has been shown to be positively correlated with PMS.

Reid and Yen (1981, Am. J. Obstet. Gynecol., 139(1): 96) postulated an aberrant release of or sensitivity to alpha-MSH and beta-endorphins during the luteal phase of the menstrual cycle as triggering a number of neuroendocrine changes responsible for PMS.

Other recent evidence has been advanced to suggest that PMS is related to neuroendocrine function. Muse et al. (1984, N. Engl. J. Med. 311: 1345-1349) in 1984 reported the effective and beneficial treatment of medical ovariectomy-reversible ovarian failure induced by a gonadotrophin releasing hormone agonist. In a crossover study, 8 patients were relieved by daily administration of a gonadotrophin releasing hormone agonist. Although the use of gonadotrophin releasing hormone agonists seemed to have a physiologic effect on the symptoms of PMS, the clinical practicality of this treatment for individuals with less than disabling symptoms of PMS is questionable because of undesirable consequences such as osteoporosis.

Today physicians are faced with an array of therapeutic modalities ranging from diuretics, to vitamins, to hormonal suppositories. The most popular approaches have involved vitamin $B_6$ and progesterone supplementation. Yet, double-blind, placebo-controlled trials have not substantiated the benefit or effectiveness of any one treatment.

Premenstrual syndrome, as noted above, encompasses a broad spectrum of symptomatology that is probably related to a vascular and smooth muscle responsiveness or to hormonal secretion. Premenstrual headache might be explained as a primary vasospastic event; abdominal cramps possibly as smooth muscle hyperexcitability. Calcium has been shown to have a role in the release of neurotransmitters, endocrine and exocrine products, in the contraction of skeletal and smooth muscle, and metabolism. Calcium's importance has been shown at the biochemical level, but its clinical application as a supplement or therapeutic modality other than for the known entities such as tetany/hypocalcemia has never been shown. Supplemental calcium's use in vascular headache, abdominal menstrual cramps, and PMS has never been studied. The precise role of calcium in the pathophysiology of PMS is not known, and whether the interaction of calcium is with ovarian linked hormones or with neuroendocrine modulators is unclear. As menstruation is related to ovarian and pituitary secretory function, it is not unreasonable to postulate a calcium-linked hormonal effect on those behavioral and somatic changes that occur during this period. Calcium coupled with these hormones may modulate the intrinsic feedback mechanisms that translate physiologic neuroendocrine and hormonal messages into behavioral and somatic changes.

BRIEF DESCRIPTION OF THE FIGURE

FIG. 1 shows the total mean symptom scores (±S.E.M.) during luteal and menstrual phases for Group 1 (placebo first) and for Group 2 (calcium first). Month 0 represents the pre-treatment phase, months 1-6 represents the treatment phase on calcium and placebo, and month 7 represents the post-treatment phase. The solid arrow and break in the line indicate crossover at the end of the 3rd month of treatment.

SUMMARY OF THE INVENTION

The present invention is directed to a method for the treatment of premenstrual syndrome through the administration of calcium to an individual. Accordingly, a therapeutically effective dose of calcium is administered to an individual who manifests the symptomatology of PMS. Therapy with calcium may be commenced on the day of diagnosis regardless of when the individual's menstrual period begins and should continue until the symptoms totally abate. Should PMS symptoms recur, treatment should be resumed.

The calcium is administered in any appropriate form. In a preferred embodiment of the invention, the calcium is administered orally in the form of tablets of calcium carbonate. Other calcium compounds which should be equally as effective are calcium gluceptate, calcium gluconate, calcium lactate, calcium phosphate, calcium chloride, calcium levulinate, calcium acetate, calcium citrate and calcium stearate. Additionally, the calcium may be administered in any other appropriate manner such as transdermally. The equivalent of 1000 mg. a day of elemental calcium is an appropriate dose. However, calcium may be provided in doses ranging from 250 mg. to 2000 mg. per day.

The method of the invention is demonstrated, by way of a clinical trial, using a double-blind crossover design. It is the first trial of its kind to explore the usefulness of calcium in PMS and demonstrates a significant effect of calcium supplementation on the premenstrual and menstrual symptomatology. Efficacy was determined prospectively by changes in daily symptom scores over a 6 month period, and retrospectively by an overall global assessment. In both cases, each of these evaluations established that calcium supplementation significantly reduced physical and behavioral symptomatology in PMS. Calcium treatment had a significant benefit on premenstrual symptoms such as depression, irritability, headache, mood swings, abdominal bloating and back pain. These are the symptoms that women commonly cite as those that interfere with their daily activities. A positive effect of calcium supplementation was also noted on menstrual cramps during both the premenstrual and menstrual phases. Thus, calcium supplementation offers a simple and rational approach for women with PMS.

DETAILED DESCRIPTION OF THE INVENTION

The method of the invention involves administering a therapeutically effective dose of calcium to an individual who is identified as demonstrating mild to severe symptoms of premenstrual syndrome. The results of the clinical trial described in the example herein indicate that calcium should be administered to the individual exhibiting PMS symptomatology on the day of diagnosis regardless of when the menstrual period begins and treatment should continue until the symptoms abate. Treatment may be resumed if symptoms recur.

The calcium is administered in any appropriate form. In a preferred embodiment of the invention, the calcium is administered orally in the form of tablets of calcium carbonate. Other calcium compounds which should be equally as effective are calcium gluceptate, calcium gluconate, calcium lactate, calcium phosphate, calcium chloride, calcium levulinate, calcium acetate, calcium citrate and calcium stearate. Additionally, the calcium may be administered in any other appropriate manner such as transdermally. The equivalent of 1000 mg. a day of elemental calcium is an appropriate dose. However, calcium may be provided in doses ranging from 250 mg. to 2000 mg. per day.

In order to evaluate the efficacy of calcium supplementation in premenstrual syndrome (PMS) a randomized, double-blind crossover placebo-controlled study was conducted in 33 women. PMS symptomatology was assessed by the daily recording of fourteen symptoms as well as an overall retrospective analysis. Only women with symptom scores during the late luteal phase that were at least 50% greater than the intermenstrual phase were selected. The two modalities of evaluation established that calcium supplementation significantly reduced PMS symptomatology. In the retrospective assessment of overall symptoms, 73% of the women reported fewer symptoms during the treatment phase on calcium, 15% preferred placebo and 12% had no clear preference. Multivariate repeated measures analysis of variance on symptom ratings derived from daily PMS symptom scores confirmed this reduction in symptomatology on calcium treatment during both the luteal ($p=0.011$) and the menstrual phases ($p=0.032$) of the reproductive cycle. Calcium supplementation had no effect during the intermenstrual phase. Three premenstrual factors [negative affect ($p=0.045$), water retention ($p=0.003$), pain ($p=0.036$)], and one menstrual factor [pain ($p=0.02$)] were shown to significantly improve on calcium. Calcium supplementation is a simple and effective treatment for premenstrual syndrome, but further studies will be needed to determine its precise role in PMS.

Separate analyses on luteal and menstrual symptomatology were purposely conducted in light of the current controversy over the definition of PMS and demonstrated calcium supplementation to be effective in both of these phases of the menstrual cycle. Of note, in the selection of study participants, is that only women with luteal symptoms with a symptom free intermenstrual phase were included whether or not menstrual symptoms were present, and those women with solely menstrual symptoms in the absence of luteal symptoms were excluded. Hypothetically, the absence of luteal symptomatology should preclude the diagnosis of PMS, while the presence of both luteal and menstrual symptomatology should not. The observation that calcium supplementation was effective in both of these phases might support those investigators who claim that menstrual symptomatology is as important as luteal symptomatology in PMS.

EXAMPLE

Enrollment and assignment of participants

The study described herein was conducted at Metropolitan Hospital in New York City between January 1986 and February 1987. The protocol was approved by the Committee for Protection of Human Subjects in November 1985. Seventy-eight participants with a self diagnosis of PMS were recruited from the hospital staff and from outpatient volunteers of the primary care clinic populations. Informed consent was obtained from all subjects.

Women were selected if they fulfilled a strict definition of premenstrual syndrome: cyclically recurring symptoms during the luteal phase of the menstrual cycle with a symptom free period following menses. All had related a chronicity of symptoms during this time. Each woman was asked to complete daily pre-trial self assessment questionnaires where 14 daily symptoms were recorded and measured over one menstrual cycle. Each was instructed to complete one questionnaire every evening, describing how she felt during the previous 24 hours. The 14 symptoms evaluated were: nervousness, irritability, crying, mood swings, depression, fatigue, violent tendencies, abdominal bloating, headache, breast fullness, increased appetite, abdominal cramps, back pain, and craving for sweets. Each symptom was marked daily on a 4 point scale (absent, mild, moderate, or severe) and subsequently scored from 0 to 3. A symptom assessment with a 4 point rating scale similar to that previously described by Muse was used.

Women were selected if:

(1) their mean symptom scores from the latter half of the luteal phase were at least 50% greater than for the intermenstrual phase (the days following the menstrual period), (2) luteal symptoms in the latter half of the menstrual cycle were recorded as at least moderate to severe in character, and (3) they agreed to refrain from the use of analgesics, specifically nonsteroidal anti-inflammatory agents, during this period.

Criteria for exclusion from the clinical trial were: (1) elevated luteinizing hormone or follicular stimulating hormone levels (levels were drawn on days 1–5 of the menstrual cycle), renal insufficiency, (3) history of renal colic, nephrolithiasis, hyperparathyroidism, (4) involvement in an investigational drug study within four weeks of entry, (5) presence of active peptic ulcer disease, achlorhydria, inflammatory bowel disease, malabsorption, (6) digitalis therapy, (7) history of endometriosis, (8) pregnancy, (9) use of calcium channel blockers or thiazides, (10) mental retardation, (11) recent menometrorrhagia or menorrhagia.

The preliminary evaluation on each patient included:

(1) A standardized patient history and detailed gynecological history as well as a routine physical examination including the gynecologic examination.

(2) Dietary Assessment

Each woman was given a packet of seven dietary forms and instructed to list her daily meals for one week. Each had been carefully counselled as to the recording of accurate proportions. The mean dietary calcium intake was then assessed and calculated by the Director of dietary services at the hospital.

(3) Laboratory

All women had a complete blood count, SMA-18 and urinalysis before introduction to treatment. Baseline serum follicular stimulating hormone and luteinizing hormone levels were determined by radioimmunoassay and were within the premenopausal range for all women selected. After the 3rd and 6th months of the treatment phase, serum calcium determinations were repeated and all were within normal laboratory limits. All laboratory evaluations were performed by a single central laboratory (Metpath in Teterboro, N.J.).

All women were evaluated by two staff psychiatrists prior to entry into the study. Each participant was screened using a standardized mental status evaluation. On the basis of the psychiatric interview, it was established that all participants were euthymic. Any woman with active major depression or a history of psychosis was excluded from the study.

All women who met the criteria of premenstrual syndrome and qualified for the trial were enrolled in the study.

STUDY PROTOCOL AND FOLLOW-UP OBSERVATIONS

The study was designed in a double-blind crossover manner. Symptom scores were initially measured daily over one menstrual cycle prior to treatment (baseline), measured through the two part treatment phase (six cycles), and then measured for one additional menstrual cycle off medication. Women were randomly assigned in a double-blind fashion to one of 2 groups. The subjects in Group 1 were initially begun on placebo for 3 months and crossed over to calcium; those of Group 2 were begun on elemental calcium and crossed over to placebo. Crossover occurred at the end of the menstrual phase into the fourth menstrual cycle, and the women were followed for another three menstrual cycles into the beginning of the seventh menstrual cycle. Each woman began treatment on the first day after her menstrual period and was monitored regularly at one month intervals for the subsequent seven months by the investigators. Each was given a bottle of seventy tablets with instructions to take two tablets a day (the equivalent of 1000 mg of elemental calcium a day provided in the form of calcium carbonate). Each was supplied monthly, with a loose leaf binder containing a set of 35 questionnaires listing the 14 PMS symptoms, and directed to daily record the level of severity of her symptoms. At all follow-up visits, subjects were questioned as to response to medication, onset of the menstrual period, days of menstrual flow, presence of blood clots, and drug related side effects. Daily symptom scores on the 14 PMS symptoms were added up for a total symptom score by the investigators. A final assessment was made during the post-treatment phase where the women were asked if their overall symptoms improved during the first or second treatment phase of the study.

All medications (Oscal 500 and placebo) were supplied by Marion Laboratories. The corresponding placebo tablet was identical in appearance and similar in taste to the active medication. All medications were packaged, labelled and dispensed in a double blind manner by the hospital pharmacy in quantities of 70 tablets per bottle or approximately one month's supply. All pharmacists involved in the actual dispensing of the medication were ignorant of the randomization.

COMPLIANCE

Compliance with the treatment regimen was assessed at each 4 week visit by tabulating the remaining number of medications. Women were routinely contacted at biweekly intervals by a research nurse or the investigators to check compliance and adherence to the protocol. Any woman with less than 70% overall compliance was excluded from the study. Any woman who took fewer than 70% of the tablets for a given month was asked to repeat the month on the same medication with the initial data excluded from the statistical analysis.

DATA ANALYSIS

Quantitative baseline differences between the two treatment groups were compared using the t-test analysis for continuous variables and the chi-square statistic for categorical variables. Mean symptom scores were derived from the daily symptom ratings for the various phases of the menstrual cycle as follows:

luteal phase—the 7 days prior to the menstrual period
menstrual phase—the days of menstruation
intermenstrual phase—the 7 days following the menstrual period Repeated measures analysis of variance was conducted to test the efficacy of calcium supplementation on symptomatology. Baseline symptom scores were used as covariates. The strength of the design and analysis of our study was that each woman served as her control. The primary contrast of interest was whether a woman felt better on calcium as compared to placebo. Three factors were entered in the analysis. The calcium treatment factor tested for the efficacy of the calcium within each subject. The treatment group factor (calcium-placebo versus placebo-calcium) tested the effect of order on symptom scores. The cycle factor (3 cycles within each treatment phase) was transformed using orthogonal polynomials in order to test whether symptomatology improved linearly or quadratically during the three cycle period. Two tailed tests of significance were applied and results were considered significant at $p$ values $<0.05$.

A factor analysis was performed to empirically determine which symptoms could be combined to come up with subgroups or clusters of symptoms. The factor analysis was done on 2413 daily symptom ratings during the luteal and menstrual phases with at least one symptom present. Multiple records per individual were analyzed since the sample was too small to allow the use of one rating per woman. Based on visual inspection of a screen plot of eigenvalues, and subsequent examination of the content and face validity of the factors, four factors were extracted using principal components analysis. The four factors were rotated using the varimax method, which attempts to minimize the number of items with high loadings on a factor. Factor loadings of 0.45 and over were required for a symptom to be considered as belonging to a factor. Repeated measures analysis of variance was performed with scores on the 4 factors as outcome data.

RESULTS

Patient Characteristics

Of the 78 women initially screened, 60 were enrolled. Among the 18 subjects who did not qualify for the program, the reasons were failure to meet the definition of PMS (N=12), pregnancy (N=2), active peptic ulcer disease (N=1), mental retardation (N=1), menometrorrhagia (N-1), and undiagnosed abdominal pain (N=1). Of the 60 women who entered the study, 27 discontinued participation before treatment crossover, yielding a total of 33 women with complete data for analysis. The reasons for discontinuation were: refusal to crossover due to marked clinical improvement (N=2, Group 2), no benefit on the study medication and refusal to continue (N=3, Group 1), failure to collect the study medication (N=6, Group 2; N=3, Group 1), noncompliance (N=4, Group 2; N=2, Group 1, pregnancy (N=1, Group 2), alcoholism and hypocalcemia (N=1, Group 2) and lost to follow-up (N=2, Group 1). Twenty-two of the 33 women received at least 90% of the prescribed medication. A total of 209 monthly cycles were recorded during the treatment phase; 11 cycles were eliminated and 198 cycles (33 women×6 treatment cycles) analyzed. The majority of subjects were New York City Hospital employees in health related fields, e.g., nurses, health educators, nurses aides. Most were Black (N=14) or Hispanic (N=12) while 2 were Caucasian and 5 were Oriental. The mean age of the women was 35 and ranged from 26 to 48 years; the mean age at menarche was 12 years. Forty-eight percent of the women described recent worsening of premenstrual symptoms as well as marked worsening following pregnancy. Background characteristics are listed in Table 1 below. In the majority of symptoms reported during the pretreatment baseline period manifested during the luteal and menstrual phases (the perimenstrual phase) of the reproductive cycle. As seen in Table 2 below, these perimenstrual symptom specific means were at least 1.5 to 17 fold greater than the intermenstrual means with a nearly equivalent prevalence of symptoms for the luteal and menstrual phases for irritability, nervousnness, mood swings, depression, fatigue, headache, violent tendencies, abdominal bloating, breast fullness and craving for sweets. Because of this, the symptoms in the menstrual phase were considered an integral and significant part of the woman's symptoms. However, due to the current theoretical controversy in the definition of PMS, our statistical analysis separated out these 2 phases.

TABLE 1

Background Characteristics of Thirty-three Women with Premenstrual Syndrome*

|  | Group 1 | Group 2 | Total |
|---|---|---|---|
| Age (years) | 34.6 ± 6.5 | 35.9 ± 5.3 | 35.1 ± 6.0 |
| Age at menarche | 12.2 ± 2.4 | 12.6 ± 1.1 | 12.4 ± 2.0 |
| Approximate cycle length (days) | 27.6 ± 2.4 | 28.1 ± 2.1 | 27.8 ± 2.3 |
| History of menometrorr-hagia (%) | 37% | 21% | 30% |
| History of menorrhagia (%) | 22% | 14% | 19% |
| Use of contraceptives | 37% | 57% | 45% |
| Number of pregnancies | 1.7 ± 1.7 | 1.9 ± 1.4 | 1.79 ± 1.6 |
| Number of term pregnancies | .89 ± 1.2 | 1.2 ± 1.1 | 1.0 ± 1.2 |
| Number of abortions | .79 ± 1.3 | .64 ± 1.0 | .73 ± .9 |
| Number of children | .76 ± 1.3 | 1.5 ± 1.6 | 1.07 ± 1.4 |
| Number of years of PMS | 16.6 ± 8.0 | 16.2 ± 9.0 | 16.4 ± 8.3 |
| PMS worsening recently (%) | 53% | 43% | 48% |
| PMS worsening after pregnancy | 55% | 40% | 48% |
| Height (cm) | 162.0 ± 7.8 | 162.6 ± 4.9 | 162.2 ± 6.8 |
| Weight (kg) | 64.4 ± 12.3 | 60.4 ± 8.18 | 62.7 ± 10.7 |
| Baseline calcium 9.51 ± .26 mg/dl** | 9.60 ± .24 | 9.37 ± .22 | *** |
| 3rd month calcium | 9.39 ± .33 | 9.30 ± .37 | 9.35 ± .34 |

*Data are expressed as mean ± standard deviation or percentages for yes/no answers
**To convert milligrams per deciliter to millimoles per liter, multiply by .2495
***p = .006

TABLE 2

Baseline Mean Specific Symptom Scores

| Symptom | Intermenstrual mean | Luteal mean | Menstrual mean |
|---|---|---|---|
| nervousness | .07 ± .18 | .27 ± .38 | .37 ± .53 |
| irritability | .06 ± .14 | .58 ± .60 | .68 ± .73 |
| crying | .05 ± .15 | .09 ± .22 | .21 ± .40 |
| mood swings | .07 ± .14 | .48 ± .65 | .52 ± .66 |
| depression | .07 ± .17 | .43 ± .59 | .49 ± .63 |
| fatigue | .26 ± .33 | .75 ± .62 | .80 ± .88 |
| violent tendencies | .0 ± .0 | .13 ± .40 | .18 ± .57 |
| abdominal bloating | .06 ± .13 | .74 ± .68 | .86 ± .86 |
| headache | .29 ± .34 | .52 ± .46 | .83 ± .79 |
| breast fullness | .09 ± .36 | .81 ± .69 | .84 ± .84 |
| increased appetite | .11 ± .30 | .55 ± .66 | .38 ± .64 |
| abdominal cramps | .02 ± .05 | .34 ± .43 | .99 ± .87 |
| back pain | .06 ± .11 | .49 ± .63 | .97 ± .99 |
| craving for sweets | .14 ± .30 | .51 ± .64 | .69 ± .76 |

Values shown are means ± standard deviations

Outcome

The analysis included 33 women, 19 in Group 1 who received placebo during the first treatment phase and 14 in Group 2 who received calcium first. Table 1 lists the background characteristics of the women in the data analysis. The only statistically significant difference between the groups was in baseline calcium levels. The mean baseline calcium level in Group 1 was 9.6 mg/dl (2.4 mmol/l) and in Group 2 was 9.4 mg/dl (2.3 mmol/l). This difference was small and was within normal laboratory limits. Repeat serum calcium levels at 3 month intervals during the treatment phase were normal for all women and not significantly different. The average daily calcium intake was calculated at 531 mg (a level well below recommended intake) with a low intake of 264 mg and a daily high intake of 1726 mg. All women except one had a dietary calcium intake of less than 1000 mg a day.

In the retrospective assessment of overall improvement of symptoms (Table 3 below) in which study participants were asked during which treatment phase they experienced fewer symptoms, 73% of the women (95% Confidence Interval=56,89) said they experienced fewer symptoms during the treatment phase on calcium. Assuming that women would indicate preference by chance, we expect 33% of the women to prefer the calcium treatment. The proportion of women preferring calcium was clearly above that expected by chance as indicated by the 95% confidence interval with a lower limit of 56%. Only 15% of the women preferred the placebo phase and 12% had no clear preference. Of the women who received calcium first (Group 2), 10 cited improved symptomatology on calcium with 1 preferring placebo and 3 stating no preference. In Group 1, which received placebo first, 14 claimed benefit while on calcium with 4 preferring placebo, and 1 stating no preference. Many women described a marked improvement in breast tenderness and swelling, in headaches and in abdominal cramps over the course of the study without the need for analgesics. Many also described a loss of the 'premenstrual aura' on calcium treatment with an abrupt onset of their menstrual period without their usual forewarning symptoms.

TABLE 3

Women's Phase Preference

| Group | Total | None | Calcium | Placebo |
|---|---|---|---|---|
| 1 | 19 | 1 | 14 | 4 |
| 2 | 14 | 3 | 10 | 1 |

TABLE 3-continued

| | Women's Phase Preference | | |
|---|---|---|---|
| Group | Total | None | Calcium Placebo |
| Total | 33 | 4 | 24* 5 |

*73% (Confidence Interval = 56,89)

Repeated measures analysis of variance confirmed the above analysis of retrospective preference. Table 4 below shows the total mean symptom scores for the luteal, menstrual and intermenstrual phases. While there was an expected decrease in total mean scores on placebo, the decrease in symptomatology due to calcium treatment was significantly greater than the placebo effect during both the luteal (p=0.011) and menstrual phases (p=0.032). The total means symptom score for the luteal phase on calcium was 3.33 compared to 5.34 on placebo; the total mean symptom score for the menstrual phase on calcium was 4.71 compared to 6.02 on placebo. In contrast, there was no calcium effect on symptomatology during the intermenstrual phase (p=0.935). The effect of calcium and placebo on total symptom scores is illustrated in FIG. 1 where months 4, 5 and 6 for Group 1 and months 1, 2 and 3 for Group 2 represent the calcium treatment phase. The repeated measures analysis showed no significant carry over effect or cycle effect on symptomatology. Therefore, no progressive lowering of symptoms throughout the three cycles was demonstrated.

TABLE 4

Total Mean Symptom Scores for Luteal, Menstrual and Intermenstrual Phases

| Group | B | P | C | B | P | C | B | P | C |
|---|---|---|---|---|---|---|---|---|---|
| 1 | 8.00 | 6.25 | 3.68 | 10.03 | 7.40 | 5.47 | 1.70 | 1.43 | 1.21 |
| 2 | 4.95 | 4.11 | 2.84 | 6.94 | 4.14 | 3.68 | .85 | .94 | 1.19 |
| Total | 6.71 | 5.34 | 3.33 | 8.72 | 6.02 | 4.71 | 1.34 | 1.22 | 1.39 |
| pvalue | | | .011 | | | .032 | | | .935 |

B refers to baseline mean symptom scores
P refers to mean symptom scores on placebo;
C refers to mean symptom scores on calcium In order to better specify the effect of calcium, a factor analysis was performed on the 14 PMS symptoms. Factor 1 represented nervousness, irritability, crying, mood swings, depression and violent tendencies; factor 2 represented fatigue, abdominal bloating, headache and breast fullness, factor 3 represented increased appetite, craving for sweets; and factor 4-abdominal cramps and back pain. Each of these factors except for factor 3 replicated the factor analysis done by Moos with his subgroup classification of 46 symptoms: factor 1 being the negative affect group, factor 2 the water retention group, and factor 4 the pain group. Factor 3 was not included by Moos in his analysis.

Factor based scores were computed by taking the unweighted means of the symptom which loaded on a factor. Repeated measures analysis was then used to test for the efficacy of calcium treatment on the 4 symptom factor scores. As shown in Table 5, calcium treatment had a significant effect during the luteal phase on factor 1 (p=0.045), factor 2 (p=0.003) and factor 4 (p=0.036). During the menstrual phase, only factor 4 was significantly affected by calcium (p=0.02). As with the analysis of total scores, there was no effect of calcium on intermenstrual symptomatology.

TABLE 5

P Values for Calcium Treatment Effect on the Four Factors

| Factor | Symptoms | Luteal phase | Menstrual Phase |
|---|---|---|---|
| 1 | nervousness irritability crying mood swings depression violent tendencies | .045 | .056 |
| 2 | fatigue abdominal bloating headache breast fullness | .003 | .150 |
| 3 | increased appetite (craving for sweets) | .127 | .114 |
| 4 | abdominal cramps back pain | .036 | .021 |
| Total | All 14 symptoms | .011 | .032 |

Data represent p values with significance defined at <.05.

The daily calcium supplementation of 1000 mg was generally well tolerated by all 33 women and none of the women discontinued their participation in the study because of adverse effects. The major side effects noted during the study were nausea (N=5), constipation (N=4), flatulence (N=1), and gastrointestinal discomfort (N=3).

The present invention is not to be limited in scope by the embodiment disclosed in the example which is intended as a single illustration of one aspect of the invention and any methods which are functionally equivalent are within the scope of this invention. Indeed, various modifications of the invention in addition to those shown and described herein will become apparent to those skilled in the art from the foregoing description. Such modifications are intended to fall within the scope of the appended claims.

What is claimed is:

1. A method for treating premenstrual syndrome comprising administering to an individual in need of said treatment an effective dose of elemental calcium so that the symptoms of premenstrual syndrome are significantly reduced.

2. The method according to claim 1 in which the dose of calcium is between 250 to 2,000 mg. per day.

3. The method according to claim 2 in which the dose of calcium is 1000 mg. per day.

4. The method according to claim 1 in which the calcium is administered orally.

5. The method according to claim 1 in which the calcium is administered transdermally.

6. The method according to claim 1 in which the calcium is administered in the form of a calcium salt selected from the group consisting of calcium carbonate, calcium gluceptate, calcium gluconate, calcium lactate, calcium phosphate, calcium chloride, calcium levulinate, calcium acetate, calcium citrate, and calcium stearate.

* * * * *